(12) United States Patent
Gruca

(10) Patent No.: US 9,217,729 B2
(45) Date of Patent: Dec. 22, 2015

(54) FLOATING HEAD CONTOUR FOLLOWING HOLDER FOR ULTRASONIC TESTING

(75) Inventor: Karl M. Gruca, Palm Beach Gardens, FL (US)

(73) Assignee: United Technologies Corporation, Hartford, CT (US)

( * ) Notice: Subject to any disclaimer, the term of this patent is extended or adjusted under 35 U.S.C. 154(b) by 506 days.

(21) Appl. No.: 13/604,018

(22) Filed: Sep. 5, 2012

(65) Prior Publication Data

US 2014/0060194 A1    Mar. 6, 2014

(51) Int. Cl.
  *G01N 29/26* (2006.01)
  *G01N 29/22* (2006.01)
  *G01N 29/265* (2006.01)
  *G01N 29/28* (2006.01)

(52) U.S. Cl.
  CPC ............ *G01N 29/225* (2013.01); *G01N 29/265* (2013.01); *G01N 29/28* (2013.01); *G01N 2291/2694* (2013.01)

(58) Field of Classification Search
  CPC ... G01N 29/225; G01N 29/265; G01N 29/28; G01N 2291/2694; G01N 2291/2638; G01N 29/226; G01N 29/4463; G01N 27/902; G01N 29/0609; G01N 29/069; G01N 29/043; G01N 29/223; G10K 11/004

USPC .......... 73/620, 627, 628, 629, 632, 633, 634, 73/635, 639, 602, 618, 625, 626, 624, 73/866.5; 600/437, 439, 446, 459; 601/2, 601/4; 310/317, 319, 322
See application file for complete search history.

(56) References Cited

U.S. PATENT DOCUMENTS

| | | | |
|---|---|---|---|
| 4,970,907 A | | 11/1990 | Flynn |
| 5,392,652 A | * | 2/1995 | Levesque et al. ............... 73/629 |
| 5,576,492 A | * | 11/1996 | Phalin ............................. 73/634 |
| 6,220,099 B1 | * | 4/2001 | Marti et al. ..................... 73/633 |
| 7,946,986 B2 | | 5/2011 | Bockenstedt et al. |

OTHER PUBLICATIONS

International Search Report and Written Opinion for related International Application No. PCT/US2013/43990; report dated Aug. 22, 2013.

* cited by examiner

*Primary Examiner* — Daniel S Larkin
(74) *Attorney, Agent, or Firm* — Miller, Matthias & Hull LLP

(57) ABSTRACT

An ultrasonic transducer holder with a floating head is disclosed. This transducer holder allows the waterpath of the ultrasonic signal to be maintained over a contoured surface. Maintaining a constant waterpath between a transducer and the piece being inspected allows for inspection of surfaces that normally would not be capable of inspection by prior ultrasonic transducer holders.

18 Claims, 3 Drawing Sheets

FLOATING HEAD CONTOUR FOLLOWING HOLDER FOR ULTRASONIC TESTING

STATEMENT OF GOVERNMENT INTEREST

The United States Government has certain rights in this invention pursuant to contract number 5117182 between the United States Air Force and United Technologies Corporation.

FIELD OF DISCLOSURE

The present disclosure generally relates to testing equipment, and more specifically relates to the inspection of equipment and materials immersed in a liquid by ultrasonic signals.

BACKGROUND

Ultrasonic testing has become a popular method for flaw detection in new, as well as in-service, materials and equipment. Such testing can determine the size and position of most flaws in the material and equipment. These flaws can be surface cracks, imbedded cracks, voids in the material, non-uniform or non-desirable density, and the like. This information has allowed technicians to determine whether the inspected equipment is still in working condition and potentially how long the equipment will remain in working condition.

One industry which has benefitted greatly from ultrasonic testing has been aircraft manufacturing and maintenance. Modern aircraft require high accuracy parts to remain intact during operation, both on the outside and the inside. Such parts may include, but are not limited to, compressor fan blades, turbine fan blades, airfoils, and the like. Flaws in the original manufacture, or due to subsequent damage from use, of such parts could result in the parts not functioning properly and damaging themselves or the rest of the aircraft. Ultrasonic testing allows such potentially harmful flaws to be found before they become dangerous to the aircraft.

Ultrasonic testing begins with a transducer bombarding the object in question with sound waves. When the sound waves come upon a flaw in the object or the opposite side of the object, the wave is reflected. The transducer receives these reflected waves and turns them into an electrical signal. A computer then converts the electrical signals from the transducer into a graph that shows the size and position of the flaw.

Sound waves are transmitted better in some liquids, such as water, than in air. Thus, to increase the sensitivity of the scans, the object in question can be immersed in a tank of water or other suitable medium. The transducer is also submerged to create a waterpath, a path between the transducer and the object through the water.

The transducers are typically held by a transducer holder, which is attached to an actuator by a connection rod. This actuator allows for the transducer holder to be moved in a variety of directions, such as, but not limited to, along an axis parallel to the connection rod and along two axes perpendicular to the connection rod. The actuator may be controlled by a computer operating a pre-programmed algorithm.

While effective, the ultrasonic testing method is limited by the shape of the object being tested. Typically, the object must be relatively planar and not have complicated surface geometry. Additionally, the waterpath needs to remain constant to get consistent readings from the transducers. Clearly a need has arisen for a mechanism that would allow an operator to use ultrasonic testing to scan objects of more complex shape and design, while maintaining a constant waterpath.

SUMMARY OF THE DISCLOSURE

In accordance with one aspect of the disclosure, an ultrasonic scanning assembly having a transducer holder is disclosed. The transducer holder may include: a floating head connected to an actuator by a connection rod; at least one sliding pin slidably mounted to the floating head; a transducer block having at least one transducer mount and connected to the at least one sliding pin and being slidably mounted to the floating head; and a plurality of feet disposed on a bottom surface of the transducer block.

In a refinement, the transducer block has a rotational frame rotationally connected to the at least one slider pin and has a first rotational axis.

In a further refinement, the transducer block is rotationally connected to the rotational frame and has a second rotational axis perpendicular to the first rotational axis.

In another refinement, the transducer holder further comprises at least one transducer, each transducer disposed in a transducer mount.

In another refinement, the actuator is electronically controlled by a joystick.

In another refinement, the actuator is electronically controlled by a computer running a pre-programmed algorithm.

In yet another refinement, the transducer holder is submerged in water in an immersion tank during operation.

In yet another refinement, the at least one transducer mount is oriented such that when a transducer is mounted, the transducer points towards a smooth finished surface disposed on the transducer block. The smooth finished surface may reflect a sound wave emitted by the transducer at a known angle.

In accordance with another aspect of the disclosure, a transducer holder is disclosed. The transducer holder comprising a floating head and at least one sliding pin. The sliding pin may be slidably mounted to the floating head. The transducer holder may further include a transducer block having at least one transducer mount and connected to the at least one sliding pin and being slidably mounted to the floating head. The transducer holder may further comprise a plurality of feet disposed on a bottom surface of the transducer block.

In a refinement, the transducer block has a rotational frame rotationally connected to the at least one slider pin and has a first rotational axis.

In a further refinement, the transducer block is rotationally connected to the rotational frame and has a second rotational axis perpendicular to the first rotational axis.

In another refinement, there are exactly three feet disposed on the bottom surface of the transducer block.

In another refinement, the transducer holder further comprises at least one transducer, each transducer disposed in a transducer mount.

In yet another refinement, the transducer holder is submerged in a tank of water during operation.

In yet another refinement, the at least one transducer mount is oriented such that when a transducer is mounted, the transducer points towards a smooth finished surface disposed on the transducer block. The smooth finished surface may further reflect a sound wave emitted by the transducer at a known angle.

In yet another aspect of the disclosure, a method of ultrasonically testing an airfoil is disclosed. The method may comprise the steps of mounting an airfoil to a mount disposed inside an immersion tank; filling the immersion tank with a liquid medium, the immersion tank constructed such that a liquid may be held within the tank and around the equipment mount and having a top surface of the tank open; controlling an actuator, the actuator comprising a connection rod, by a joystick electronically connected to the actuator; and positioning a transducer holder such that a plurality of feet are in physical contact with a surface of the airfoil. The transducer holder may comprise a floating head connected to the connection rod; at least one sliding pin, slidably mounted to the floating head; a transducer block having at least one transducer mount and connected to the at least one sliding pin and being slidably mounted to the floating head; the plurality of feet disposed on a bottom surface of the transducer block; and at least one transducer, each transducer disposed in a transducer mount. The method of ultrasonically testing an airfoil may further comprise moving the transducer holder across the surface of the airfoil such that the plurality of feet are in contact with the surface of the airfoil and a constant waterpath from the at least one transducer to the surface of the airfoil is maintained; and emitting sound waves from the at least one transducer and receiving the sound waves reflected by a flaw and/or surface of the airfoil by the at least one transducer.

In a refinement, the transducer block has a rotational frame rotationally connected to the at least one slider pin and has a first rotational axis.

In a further refinement, the transducer block is rotationally connected to the rotational frame and has a second rotational axis perpendicular to the first rotational axis.

In another refinement, the actuator is controlled by a pre-programmed algorithm run on a computer electronically connected to the actuator.

In yet another refinement, the emitted sound waves are directed to the airfoil by a smooth finished surface disposed on the transducer block. The emitted sound waves are reflected by the smooth finished surface at a known angle towards the airfoil.

These and other aspects and features of the present disclosure will be better understood in light of the following detailed description when read in light of the accompanying drawings.

It should be understood that the drawings are not necessarily to scale and that the disclosed embodiments are sometimes illustrated diagrammatically and in partial views. In certain instances, details which are not necessary for an understanding of this disclosure or which render other details difficult to perceive may have been omitted. It should be understood, of course, that this disclosure is not limited to the particular embodiments illustrated herein.

DETAILED DESCRIPTION

Figure 1:
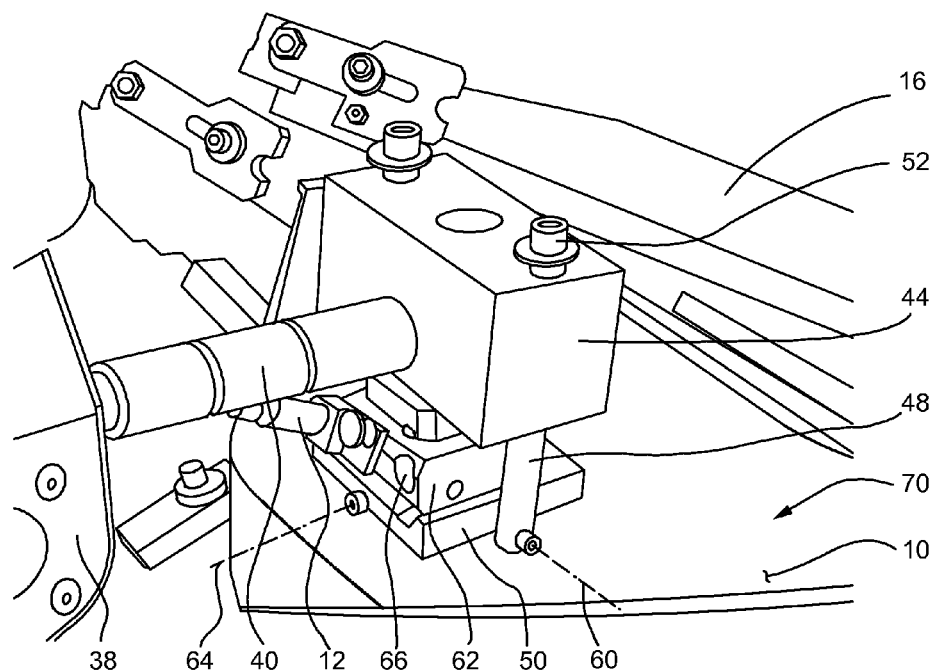
FIG. 1 is a perspective view of an airfoil being ultrasonically tested by a transducer mounted in a transducer holder constructed in accordance with the present disclosure.

Referring now to the drawings, and with specific reference to FIG. 1, a perspective view of an ultrasonic scan of a piece of equipment, specifically an airfoil 10, in progress by a transducer 12 mounted in a transducer holder 14 is shown. The airfoil 10 is supported by a mounting 16 inside an immersion tank 18. The immersion tank 18 can be filled with water or another suitable medium which will allow for a better transmission of sound waves than in air.

Figure 2:
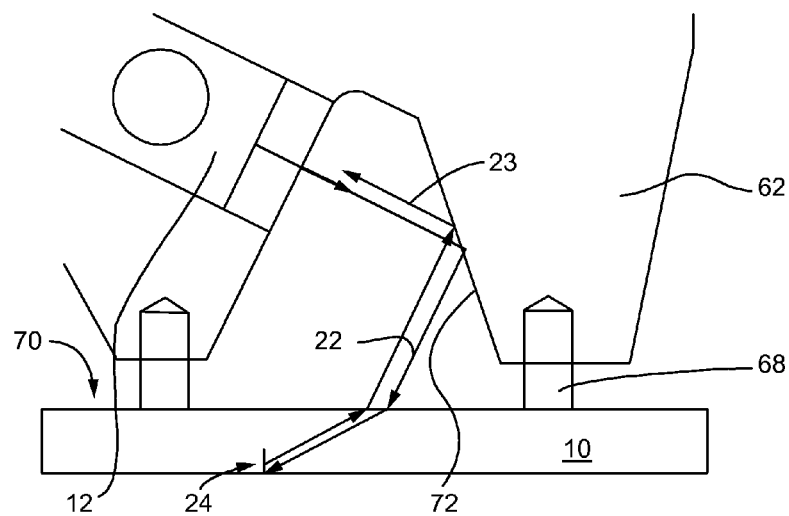
FIG. 2 is a cut-away side view of a transducer holder constructed in accordance with the present disclosure in contact with an airfoil showing the path of an emitted sound wave.

As shown in FIG. 2, when an emitted sound wave 22 comes in contact with a flaw/defect 24 the sound wave 22 may be reflected back towards the transducer 12. The transducer 12 may pick up the reflected sound wave 23 and may convert the wave into a signal which may be transmitted to a computer to be displayed as a graph.

The graph may be marked with distance marking which correspond to the distance the sound wave 22 traveled before being reflected as well as the horizontal displacement from a designated starting point. Thus, the graph may allow an operator to determine the size and position of the flaw/defect 24 in the airfoil 10.

Figure 3:
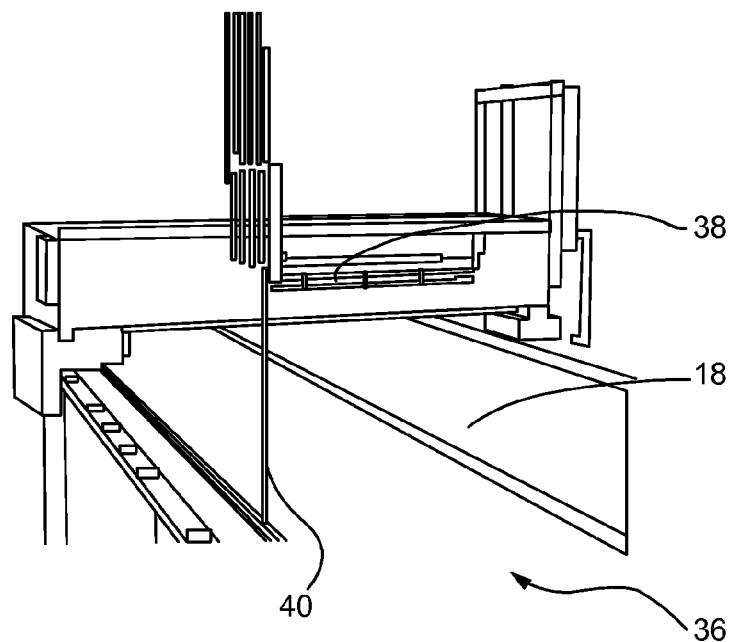
FIG. 3 is a perspective view of an immersion tank constructed in accordance with the present disclosure.

Referring now to FIG. 3, an ultrasonic scanning assembly constructed in accordance with the teachings of the present disclosure is shown and generally referred to by reference numeral 36. As shown, the ultrasonic scanning assembly 36 may be used in conjunction with the immersion tank 18. The ultrasonic scanning assembly 36 may include an actuator 38 having three degrees of motion for positioning the transducer holder 14 inside the immersion tank 18. The actuator 38 may have a connection rod 40 which may connect to the transducer holder 14 by a connection thread 42.

Figure 4:
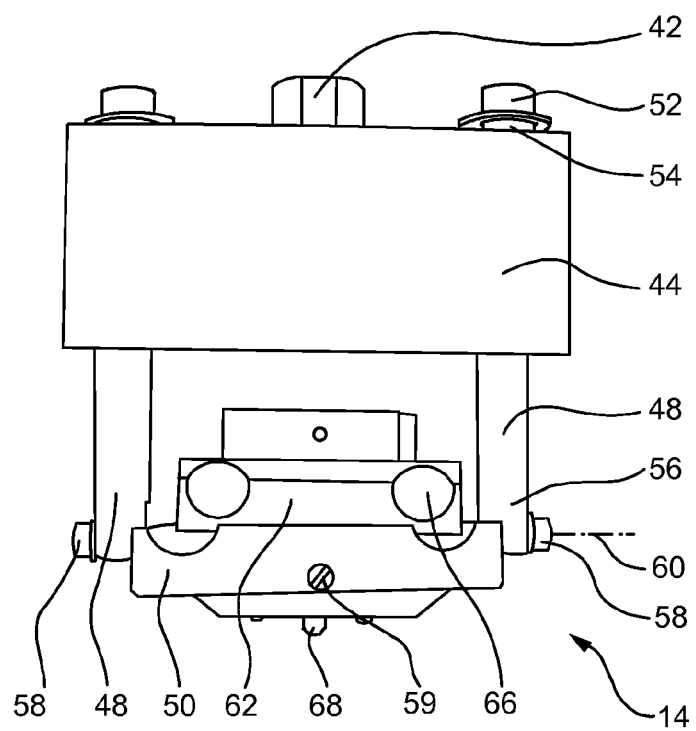
FIG. 4 is a front view of a transducer holder constructed in accordance with the present disclosure.
Figure 5:
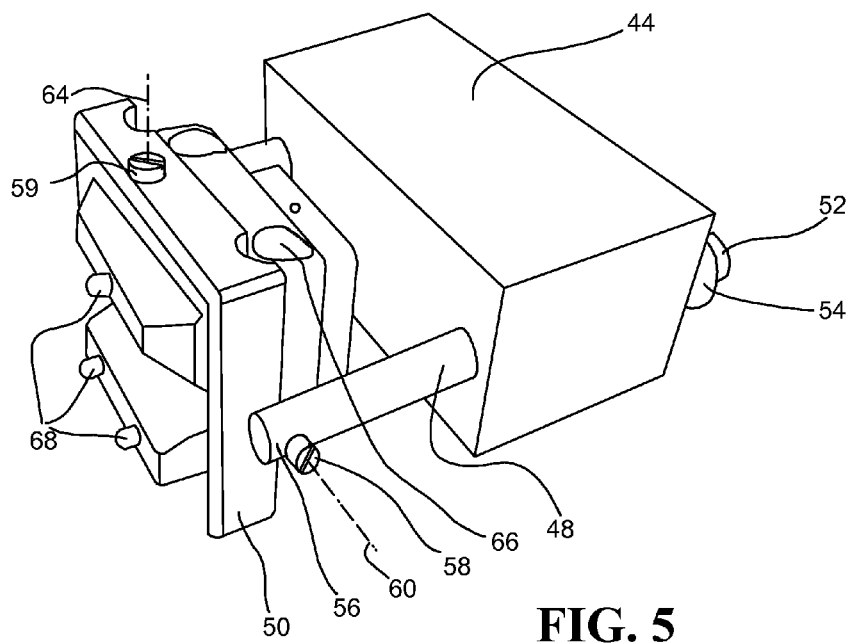
FIG. 5 is a perspective view of the transducer holder of FIG. 5.

As shown in FIG. 4 and FIG. 5, the connection thread 42 may be attached to a floating head 44. The floating head 44 may have a pair of slider holes 46 which may be used by a pair of slider pins 48 connected to a rotation frame 50. The slider pins 48 may allow the rotation frame 50 to be slidably connected to the floating head 44. The slider pins 48 may each have a slider cap 52 threadably attached at a top end 54. The slider pins 48 may further have a bottom end 56 which may each have a hinge 58 connected to the rotation frame 50. The rotation frame 50 may have free rotation provided by the hinges 58 around a first axis 60 between the pair of slider pins 48. The rotation frame 50 may further include a second pair of hinges 59 which may connect to a transducer block 62. Thus, the transducer block 62 may have limited rotation provided by the hinges 58 inside the rotation frame 50 and around a second axis 64 which may be perpendicular to the first axis 60. The rotation of the transducer block 62 around the second axis 64 is limited by the rotation frame 50.

The transducer block 62 may further have at least one mount 66 for at least one transducer 12. Each transducer 12 may transmit sound waves through the transducer block 62, through a body of water or other suitable medium, and into the material or equipment being scanned.

Figure 6:
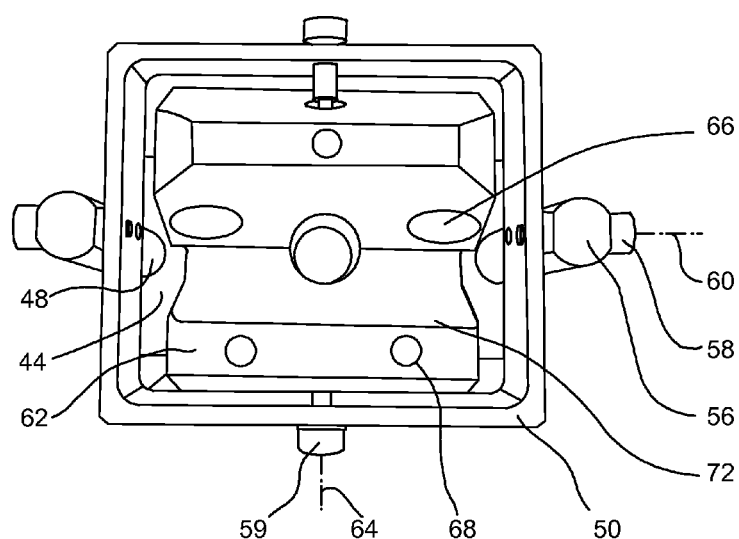
FIG. 6 is a bottom view of the transducer holder of FIGS. 5 and 6.

The underside of the transducer block 62 may have a plurality of feet 68 as shown in FIG. 6. The feet 68 may keep the transducer block 62 from coming into direct contact with the material or equipment being scanned, such as the airfoil 10. In one embodiment there are three such feet 68 disposed on the underside of the transducer block 62. The tree feet 68 define a plane which may provide a stable base for the transducer block 62 when placed onto a surface, such as a surface 70 of the airfoil 10. While three such feet 68 are shown, this is only exemplary, and any number or shape of feet may be employed.

In operation, the floating head 44 may be positioned above the surface 70 of the airfoil 10 such that the feet 68 are in contact with the surface 70. As the transducer holder 14 is moved across the surface 70 by the actuator 38 the sliding pins 48 may allow the transducer block 62 to move up and down with the contour of the airfoil 10 without the need to raise or lower the floating head 44. The rotational hinges 58 and 59 may allow the transducer block 62 to rotate to the same incline as the surface 70 as the transducer holder 14 moves. Thus, with such rotational and vertical freedom, the transducer holder 14 may be moved across the surface 70 of the airfoil 10 with the feet 68 remaining on the surface, thereby allowing the waterpath between the transducers 12 and the surface 70 to remain constant.

The actuator 38 may be controlled through a computer by an operator manipulating a joystick. The joystick may give the operator control of the actuator's three axis motion. Alternatively, the actuator 38 may be controlled by a software program programmed to follow the contours of the airfoil 10 and run on the computer.

In one embodiment, shown in FIG. 2, the transducer mounts 66 may be oriented such that when the transducers 12 are mounted, one in each transducer mount 66, the sound wave 22 is reflected off of a smooth finished surface 72 at a known calculated angle. The sound wave 22 may be reflected into the surface 70. The known angle may allow for increased accuracy when interpreting the data collected by the transducers 12 and displayed by the computer.

INDUSTRIAL APPLICABILITY

From the foregoing, it can be seen that the technology disclosed herein has industrial applicability in a variety of settings such as, but not limited to ultrasonic testing of new and in-service equipment and materials. Specifically, the testing of airfoils for use in aircraft is particularly advantageous. The present disclosure may allow the testing of airfoils and other parts with shapes or contours which were previously not possible with prior art testing apparatus. Moreover, the accuracy of the tests is increased by allowing a set of transducers to follow the contour of the airfoil, thereby allowing the transducers to maintain a constant waterpath.

The transducer block is placed in contact with the surface of the airfoil. When the transducer holder moves over the surface of the airfoil the holder is able to rotate in two directions as well as rise and fall with the contours of the surface to stay in constant contact with the surface of the airfoil. Thus, a constant waterpath between the transducers and the surface of the airfoil is maintained, allowing for more accurate data to be collected by the transducers as well as allowing for testing airfoils with more complicated geometry.

What is claimed is:

1. An ultrasonic scanning assembly having a transducer holder, comprising:
   a floating head, connected to an actuator by a connection rod;
   a plurality of sliding pins, slidably mounted to the floating head the plurality of sliding pins having a sliding pin cap attached to an end of each of the plurality of sliding pins;
   a transducer block having at least one transducer mount and connected to an opposite end of each of the plurality of sliding pins and being slidably mounted to the floating head; and
   a plurality of feet disposed on a bottom surface of the transducer block, the floating head, the plurality of sliding pins, and the transducer block being submerged in a liquid medium filling an immersion tank.

2. The ultrasonic scanning assembly of claim 1, wherein the transducer block has a rotational frame rotationally connected to the at least one slider pin and has a first rotational axis.

3. The ultrasonic scanning assembly of claim 2, wherein the transducer block is rotationally connected to the rotational frame and has a second rotational axis perpendicular to the first rotational axis.

4. The ultrasonic scanning assembly of claim 1, further comprising at least one transducer, each transducer disposed in a transducer mount.

5. The ultrasonic scanning assembly of claim 1, wherein the actuator is electronically controlled by a joystick.

6. The ultrasonic scanning assembly of claim 1, wherein the actuator is electronically controlled by a computer running a pre-programmed algorithm.

7. The ultrasonic scanning assembly of claim 1, wherein the at least one transducer mount is oriented such that when a transducer is mounted, the transducer points towards a smooth finished surface disposed on the transducer block, and the smooth finished surface reflects a sound wave emitted by the transducer at a known angle.

8. A transducer holder, comprising:
   a floating head;
   a plurality of sliding pins, slidably mounted to the floating head the plurality of sliding pins having a sliding pin cap attached to an end of each of the plurality of sliding pins;
   a transducer block having at least one transducer mount and connected to an opposite end of each of the plurality of sliding pins and being slidably mounted to the floating head; and
   a plurality of feet disposed on a bottom surface of the transducer block, the floating head, the plurality of sliding pins, and the transducer block being submerged in a liquid medium filling an immersion tank.

9. The transducer holder of claim 8, wherein the transducer block has a rotational frame rotationally connected to the at least one slider pin and has a first rotational axis.

10. The transducer holder of claim 9, wherein the transducer block is rotationally connected to the rotational frame and has a second rotational axis perpendicular to the first rotational axis.

11. The transducer holder of claim 8, wherein there are exactly three feet disposed on the bottom surface of the transducer block.

12. The transducer holder of claim 8, further comprising at least one transducer, each transducer disposed in a transducer mount.

13. The transducer holder of claim 8, wherein the at least one transducer mount is oriented such that when a transducer is mounted, the transducer points towards a smooth finished surface disposed on the transducer block and reflects a sound wave emitted by the transducer at a known calculated angle.

14. A method of ultrasonically testing an airfoil, comprising:
   mounting an airfoil to a mount disposed inside an immersion tank;
   filling the immersion tank with a liquid medium, the immersion tank constructed such that a liquid may be held within the tank and around the equipment mount; the immersion tank having an open top surface;
   controlling an actuator having a connection rod, by a joystick electronically connected to the actuator;
   positioning a transducer holder such that a plurality of feet are in physical contact with a surface of the airfoil, the transducer holder comprising:
      a floating head connected to the connection rod;
      a plurality of sliding pins, slidably mounted to the floating head the plurality of sliding pins having a sliding pin cap attached to an end of each of the plurality of sliding pins;

a transducer block having at least one transducer mount and connected to an opposite end of each of the plurality of sliding pins and being slidably mounted to the floating head; and the plurality of feet disposed on a bottom surface of the transducer block, the floating head, the plurality of sliding pins, and the transducer block being submerged in the liquid medium filling the immersion tank; and at least one transducer, each transducer disposed in a transducer mount;

moving the transducer holder across the surface of the airfoil such that the plurality of feet are in contact with the surface of the airfoil and a constant waterpath from the at least one transducer to the surface of the airfoil is maintained; and emitting sound waves from the at least one transducer directed at the airfoil and receiving sound waves reflected by a flaw and/or surface of the airfoil by the at least one transducer.

15. The method of claim 14, wherein the transducer block has a rotational frame rotationally connected to the at least one slider pin and has a first rotational axis.

16. The method of claim 15, wherein the transducer block is rotationally connected to the rotational frame and has a second rotational axis perpendicular to the first rotational axis.

17. The method of claim 14, wherein the actuator is controlled by a pre-programmed algorithm run on a computer electronically connected to the actuator.

18. The method of claim 14, wherein the emitted sound waves are directed to the airfoil by a smooth finished surface disposed on the transducer block by reflecting the sound waves at a known calculated angle towards the airfoil.

* * * * *